United States Patent
Matsumoto et al.

(10) Patent No.: US 6,409,886 B1
(45) Date of Patent: Jun. 25, 2002

(54) PROCESS FOR INHIBITING THE POLYMERIZATION OF EASILY-POLYMERIZABLE COMPOUNDS

(75) Inventors: Yukihiro Matsumoto, Kobe; Takeshi Nishimura, Himeji, both of (JP)

(73) Assignee: Nippon Shokubai Co., Ltd., Osaka-fu (JP)

( * ) Notice: Subject to any disclaimer, the term of this patent is extended or adjusted under 35 U.S.C. 154(b) by 0 days.

(21) Appl. No.: 09/549,531

(22) Filed: Apr. 14, 2000

(30) Foreign Application Priority Data

Apr. 16, 1999 (JP) .......................... 11-110043

(51) Int. Cl.$^7$ .................. B01D 3/14; C07C 51/44; C07C 57/07
(52) U.S. Cl. ............... 203/8; 203/49; 203/90; 203/DIG. 21; 562/600
(58) Field of Search ............ 203/90, 8, 2, 49, 203/1, DIG. 21; 202/158; 562/600

(56) References Cited

U.S. PATENT DOCUMENTS

| | | | |
|---|---|---|---|
| 4,256,675 A | * | 3/1981 | Vanderspurt et al. ....... 261/128 |
| 4,365,081 A | | 12/1982 | Shimizu et al. |
| 4,369,097 A | | 1/1983 | Nezu et al. |
| 4,614,827 A | * | 9/1986 | Arndt et al. ................. 556/131 |
| 4,987,252 A | * | 1/1991 | Kuragano et al. .......... 562/600 |
| 5,062,927 A | * | 11/1991 | Stout .......................... 203/89 |
| 5,159,106 A | | 10/1992 | Ritter et al. |
| 5,734,075 A | | 3/1998 | Fauconet et al. |
| 6,214,174 B1 | * | 4/2001 | Matsumoto et al. ........ 203/100 |

FOREIGN PATENT DOCUMENTS

| | | |
|---|---|---|
| DE | 2 202 980 | 7/1973 |
| EP | 0 937 488 | 8/1999 |
| WO | WO 98/12168 | 3/1998 |

* cited by examiner

*Primary Examiner*—Virginia Manoharan
(74) *Attorney, Agent, or Firm*—Wenderoth, Lind & Ponack, LLP (57) ABSTRACT

In distillation of easily polymerizable compounds such as (meth)acrylic acid and (meth)acrylic esters using a distillation unit, a liquid having substantially the same composition with that of a liquid surrounding a constitutive member placed in the distillation unit is sprayed by a spraying and supplying device. The liquid supplied by the spraying and supplying device preferably has a wetting liquid rate (of the sprayed and supplied liquid, a flow rate of a liquid attaching to and wetting the constitutive member) of 0.5 m$^3$/m$^2$hr or more relative to the surface area of the constitutive member. The liquid supplied by the spraying and supplying device preferably contains a polymerization inhibitor. It is also preferred to supply a gas containing molecular oxygen to the distillation unit. This process can effectively inhibit the polymerization of the easily polymerizable compounds, which polymerization is liable to occur inside the distillation unit.

7 Claims, 6 Drawing Sheets

PROCESS FOR INHIBITING THE POLYMERIZATION OF EASILY-POLYMERIZABLE COMPOUNDS

BACKGROUND OF THE INVENTION

1. Field of the Invention

The present invention relates to a process for inhibiting the polymerization of (meth)acrylic acid, (meth)acrylic esters, and other easily-polymerizable compounds in distillation of these compounds.

2. Description of the Related Art

Distillation is a procedure for separating components of a liquid mixture comprising two or more liquids having different boiling points. In distillation, the feedstock liquid is heated and vaporized and a vapor mainly containing a low boiling component is condensed. When the components have largely different relative volatilities, they can be easily separated. However, vaporization and condensation of only a portion of the liquid mixture cannot separate the components in expected concentrations in ordinary cases. Distillation is therefore generally performed by refluxing a portion of a condensate from the top of the column to the surface of a tray or packing in the column to ensure a vapor rising in the distillation column to thereby appropriately come in contact with a liquid flowing downward from the top, and distilling off a low boiling component from the top and withdrawing a high boiling component from the bottom of the column. Such a distillation unit for use in distillation generally includes a distillation column, a thin film evaporator, and a reactor installed a column. There may be further provided a condenser, a reboiler, and/or an external heater. The thin film evaporator may further be provided with a column on a top.

Figure 1:
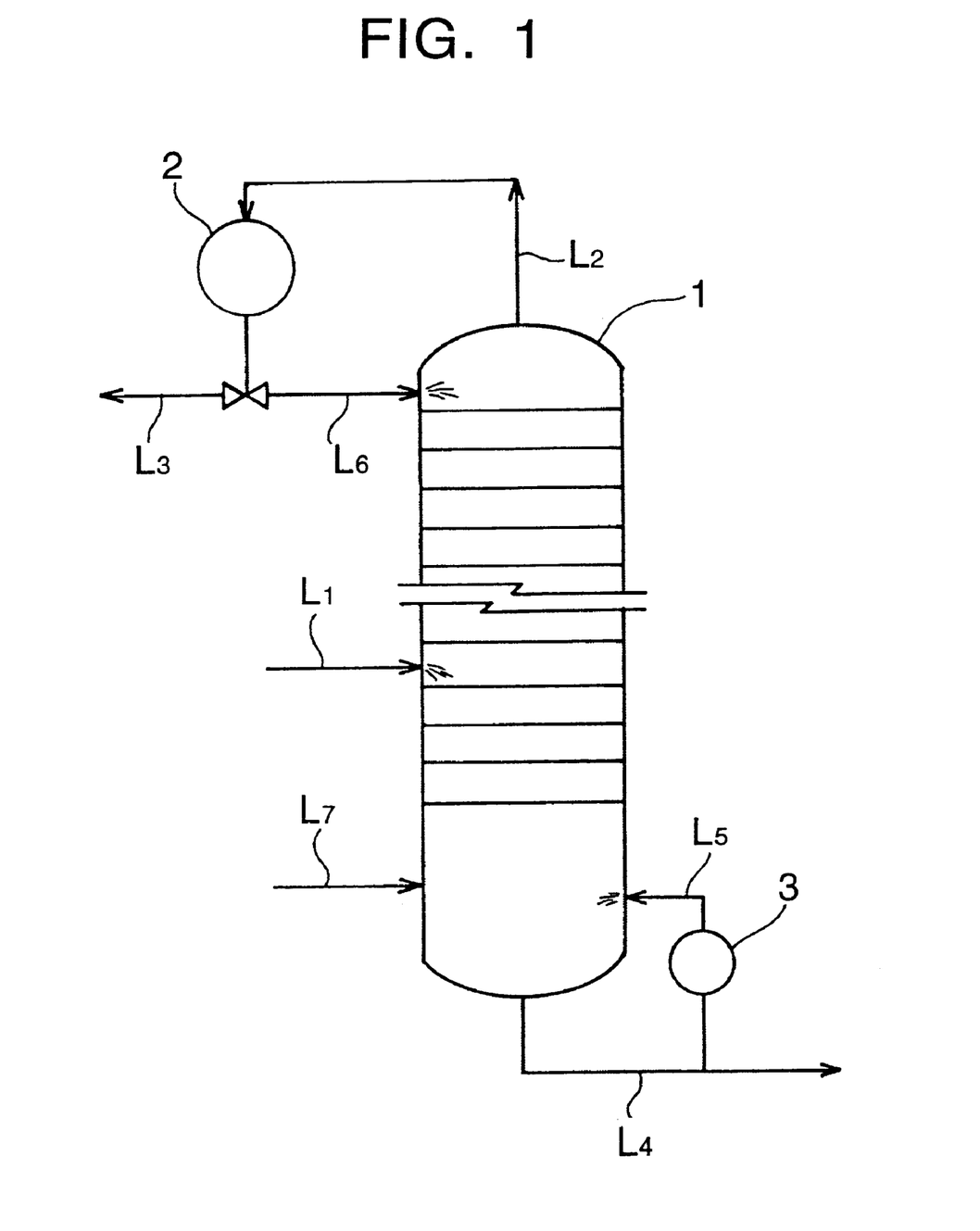
FIG. 1 is a schematic diagram illustrating a typical example of a distillation process.

FIG. 1 is an example of a cross sectional view illustrating a plate distillation column 1. Such a plate distillation column is generally used in distillation of (meth)acrylic acid and (meth)acrylic esters (hereinafter briefly referred to as "(meth)acrylic acid or its ester"). Distillation using this distillation column will now be described by taking, as an example, the use of a feedstock liquid containing the (meth)acrylic acid or its ester as a main component and acetic acid as an impurity. The feedstock liquid is supplied from a column wall into the distillation column ($L_1$). Acetic acid, a low boiling component, is vaporized by heating and rises in the column, is introduced into a condenser 2 ($L_2$) from the top of the column, is condensed, and is taken out of the system ($L_3$). Separately, a high boiling component such as the (meth)acrylic acid or its ester is fed to a subsequent step from the bottom of the column ($L_4$) as a refined liquid, and a portion of the refined liquid is returned via a reboiler 3 to the distillation column ($L_5$). The condensate contains not only the impurity acetic acid but also the (meth)acrylic acid or its ester, and a portion of the condensate is returned as a reflux liquid to the column ($L_6$), and is again subjected to gas-liquid contact in the distillation column to allow the (meth)acrylic acid or its ester to flow down to the bottom of the column.

Figure 2:
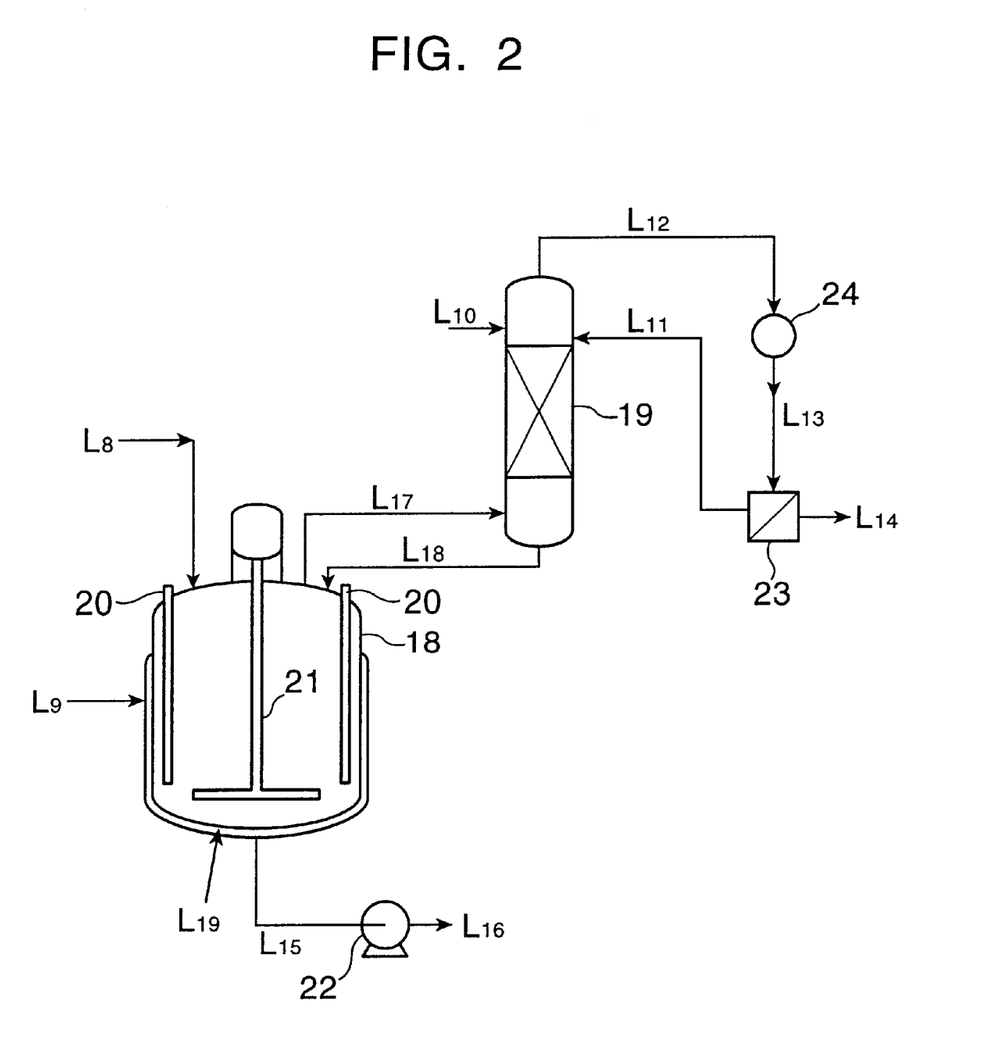
FIG. 2 is an illustrative view of a distillation unit for use in a reaction of a (meth)acrylic ester.

FIG. 2 is an illustrative view of a distillation unit for use in a reaction of a (meth)acrylic ester. As reactants, (meth) acrylic acid and a liquid containing an alcohol are fed ($L_{18}$) to a reactor 18 using an ion exchange resin, are agitated with an agitator 21 and are put ($L_9$) into a jacket of the reactor with steam for reaction, and formed water is expelled from the reactor as a vapor by distillation ($L_{17}$). A product liquid containing an esterified (meth)acrylic ester is withdrawn from an outlet ($L_{15}$) and is supplied into a succeeding purification step ($L_{16}$). The vapor from the reactor 18 is fed ($L_{17}$) to a distillation column installed on the top of the reactor 18 and is subjected to gas-liquid contact while supplying a liquid ($L_{10}$, $L_{11}$) from the top of the column. The liquid components such as the (meth)acrylic ester, (meth) acrylic acid, and alcohol fall into the reactor ($L_{18}$). A vapor distillated from the top of the column is introduced into a condenser 24 ($L_{12}$), is condensed, and is fed into a decanter 23 ($L_{13}$). After separation, a separated water phase is eliminated ($L_{14}$) and a separated oil phase is refluxed ($L_{11}$) to the distillation column 17. If necessary, the reactant alcohol is fed ($L_{10}$) from the top of the column.

The (meth)acrylic acid or its ester is highly easily polymerizable compounds, and a polymerization inhibitor such as hydroquinone or phenothiazine is generally added to the feedstock liquid mixture and/or the reflux liquid. To inhibit the polymerization, a technique of supplying a gas containing molecular oxygen from a lower part ($L_7$) of the distillation unit is also employed.

Japanese Examined Patent Publication No. 63-11921 discloses another distillation technique. Specifically external heaters, e.g., heating jackets, are provided on an evaporator above and below an evaporation surface. These external heaters inhibit vapor from condensing and polymerizing on an inner surface of a gas section of the evaporator without any polymerization inhibitor.

By these conventional techniques, however, the polymerization cannot be always inhibited, and the operation of the distillation unit is relatively frequently stopped to remove polymer, because the formation of such polymer deteriorates the purification efficiency.

SUMMARY OF THE INVENTION

The present invention has been accomplished under these circumstances, and an object of the invention is to provide a process which is capable of inhibiting the polymerization of easily polymerizable compounds such as (meth)acrylic acid and (meth)acrylic esters in a distillation unit during the distillation of these compounds.

Specifically, the invention provides a process for inhibiting the polymerization of a easily polymerizable compound in distillation of the compound using a distillation unit. In the process, a liquid is supplied to a constitutive member by a spraying and supplying means, the constitutive member is placed in the distillation unit, and the liquid has substantially the same composition with that of a liquid surrounding the constitutive member. The temperature of the liquid supplied by the spraying and supplying means may be preferably equal to or lower than that of liquid surrounding the constitutive member in the distillation unit. Further, the liquid may preferably have a wetting liquid rate (of the sprayed and supplied liquid, a volume of a liquid attaching to and wetting the constitutive member) of 0.5 $m^3/m^2$ hr or more relative to the surface area of the constitutive member. The liquid supplied by the spraying and supplying means preferably contains a polymerization inhibitor. It is also preferred to supply a gas containing molecular oxygen to the distillation unit. Oxygen gas and air may be used as the molecular-oxygen-containing gas. The proportion of the molecular-oxygen-containing gas (when the gas contains another component in addition to oxygen gas, the proportion in terms of oxygen gas) is preferably about 0.01 to 5% by volume, and more preferably about 0.02 to 3% by volume relative to the evaporation volume rate (at standard temperature and pressure) of the easily polymerizable compound in a vapor phase.

The constitutive member includes, but is not limited to, a tray supporting member, a packing supporting member, a flange, a nozzle, an end plate (e.g., a flat, dish-form, semi-elliptic, semi-spherical, or conical-form end plate), a column wall, a chimney, a downcomer, a baffle, and a shaft of an agitator. The easily polymerizable compound may be, preferably for example, (meth)acrylic acid, (meth)acrylic esters (methyl(meth)acrylate, ethyl (meth)acrylate, isopropyl (meth)acrylate, n-propyl (meth)acrylate, isobutyl (meth) acrylate, n-butyl (meth)acrylate, 2-ethylhexylacrylate, 2-hydroxyethyl (meth)acrylate, hydroxypropyl (meth) acrylate, and dialkylaminoethyl (meth)acrylates).

DESCRIPTION OF THE PREFERRED EMBODIMENT

In distillation of a easily polymerizable compound using a distillation unit, the easily polymerizable compound stagnates on the surface of a constitutive member in the distillation unit, that is, the same liquid stagnates in the same place, to generate the polymerization of the easily polymerizable compound. Particularly, when a condensed liquid of a vapor stagnates on the surface of the constitutive member, the liquid condensate contain little amount of a polymerization inhibitor to increase the amounts of polymer to thereby stop the operation in many cases.

The present inventors found that the polymerization in a distillation unit can be effectively inhibited by avoiding stagnation of a liquid on the surface of a constitutive member in distillation of a easily polymerizable compound such as (meth)acrylic acid or its ester; and that spraying of a liquid all over the surface of the constitutive member can achieve this advantage, which liquid has substantially the same composition with that of a liquid surrounding the constitutive member. The present invention has been accomplished on the basis of these findings. The liquid to be sprayed may have a temperature equal to or lower than the liquid surrounding the constitutive member. Also, the liquid may preferably contain a polymerization inhibitor. Accordingly, the above advantage is further enhanced by the presence of molecular oxygen in the distillation unit.

The liquid for spraying on the constitutive member in the distillation unit (hereinafter briefly referred to as "spray liquid") is one having substantially the same composition with that of a liquid surrounding the constitutive member. Specifically, the spray liquid may be, for example, a feed liquid (feedstock liquid), a liquid withdrawn from the unit, a reflux liquid, a bottom circulation liquid (refined liquid). A portion or the whole of the spray liquid is to be sprayed. The spray liquid should preferably has a lower concentration of the easily polymerizable compound or a lower viscosity than that of the liquid surrounding the constitutive member. To this end, the spray liquid should be preferably diluted with, for example, water, an alcohol, an azeotropic solvent, or an extraction solvent before spraying, within the range not deteriorating the operation procedure, to have a lower concentration or viscosity.

It may be preferable to spray the liquid having a temperature equal to or lower than the surrounding of constitutive member of the distillation unit. Further, it may be preferable to spray the liquid having a temperature 0° C. to 40° C., more preferably, 1° C. to 30° C., lower than the surface of the constitutive member. If the sprayed liquid has a temperature higher than the surrounding of constitutive member, a part of the sprayed liquid is likely to evaporate, consequently disturbing the sprayed liquid. On the other hand, the temperature difference between the sprayed liquid and the space near the constitutive member is more than 40° C., the gas surrounding the constitutive member is likely to condense greater, consequently loosing the polymerization inhibition.

The liquid contains, but is not limited to, preferably hydroquinone, phenothiazine, methoquinone, manganese acetate, nitrosophenol, cupferron, N-oxyl compounds, copper dibutyl thiocarbamate, as polymerization inhibitors. The polymerization inhibitor is to be dissolved in the easily polymerizable compound or in a solvent to form a solution, and the solution is to be put into a supply line of the feed liquid, reflux liquid, or bottom circulation liquid or to be directly supplied into the distillation unit. In this connection, the bottom circulation liquid generally comprises relatively large amounts of a polymerization inhibitor directly supplied to the distillation unit, and can be returned to the distillation unit and sprayed without the addition of another portion of the polymerization inhibitor.

The gas containing molecular oxygen should preferably have an oxygen concentration of higher than that of the air (20 to 21% by volume), more preferably, 40 to 100% by volume, and further more preferably, 80 to 100% by volume. When the oxygen concentration is excessively low, a large amount of the gas is required for the inhibition of polymerization to increase the required capacity of a vacuum unit, and amounts of polymer in the distillation unit and the vacuum unit are increased.

According to the invented process, the spray liquid is sprayed, by the spraying and supplying means (sprayer) to the constitutive member in the distillation unit to evenly wet the overall surface of the constitutive member. Conditions for spraying such as the type (species) of the spray, the number of nozzles, and a flow rate can be appropriately set according to, for example, the position (location) of the constitutive member, and the operating condition in the distillation unit. At least, the conditions should be preferably set to wet the overall surface of the constitutive member as evenly as possible.

Regarding the liquid rate of the spray, the wetting liquid rate is preferably about 0.5 $m^3/m^2hr$ or more, more preferably about 1 $m^3/m^2hr$ or more, and particularly about 2 $m^3/m^2hr$ or more relative to the surface area of the constitutive member. The surface area of the constitutive member is indicated by $(\pi/4)(D)^2$, where D is a diameter of the constitutive member, in flanges and nozzles, and is indicated by a wetting area calculated from the spread angle of a spray nozzle and the distance between the spray nozzle and the surface of the constitutive member, in the other constitutive members.

The constitutive members placed in the distillation unit include, but are not limited to, preferably tray supporting members, packing supporting members, flanges, nozzles, end plates, column walls, chimneys, down comers, baffles, and shafts of agitators. The term "nozzle" as used herein means and includes all nozzles and nozzle-like devices placed in the distillation unit. Such nozzles include, for example, inlet and outlet nozzles for vapor or liquid, manholes, and instrument connection (e.g., manometer connection, pressure gage connection, liquid level connection, and thermometer connection). In such constitutive members, the polymerization can be inhibited by spraying the spray liquid to regions where a liquid formed by condensation of vapor is liable to stagnate to cause the polymerization and thereby inhibiting the stagnation of the liquid. In addition, the polymerization in a liquid phase can also be inhibited by moving a stagnant liquid in the liquid phase with the aid of the spray liquid.

As easily polymerizable compounds, there may be raised (meth)acrylic acid and (meth)acrylic esters. The (meth) acrylic esters may include methyl (meth)acrylate, ethyl (meth)acrylate, isopropyl (meth)acrylate, n-propyl (meth) acrylate, isobutyl (meth)acrylate, n-butyl (meth)acrylate, 2-ethylhexylacrylate, 2-hydroxyethyl (meth)acrylate, hydroxypropyl (meth)acrylate, and dialkylaminoethyl (meth)acrylates. This invention is most useful for (meth) acrylic acid which is most easily to polymerize among these compounds.

Figure 3:
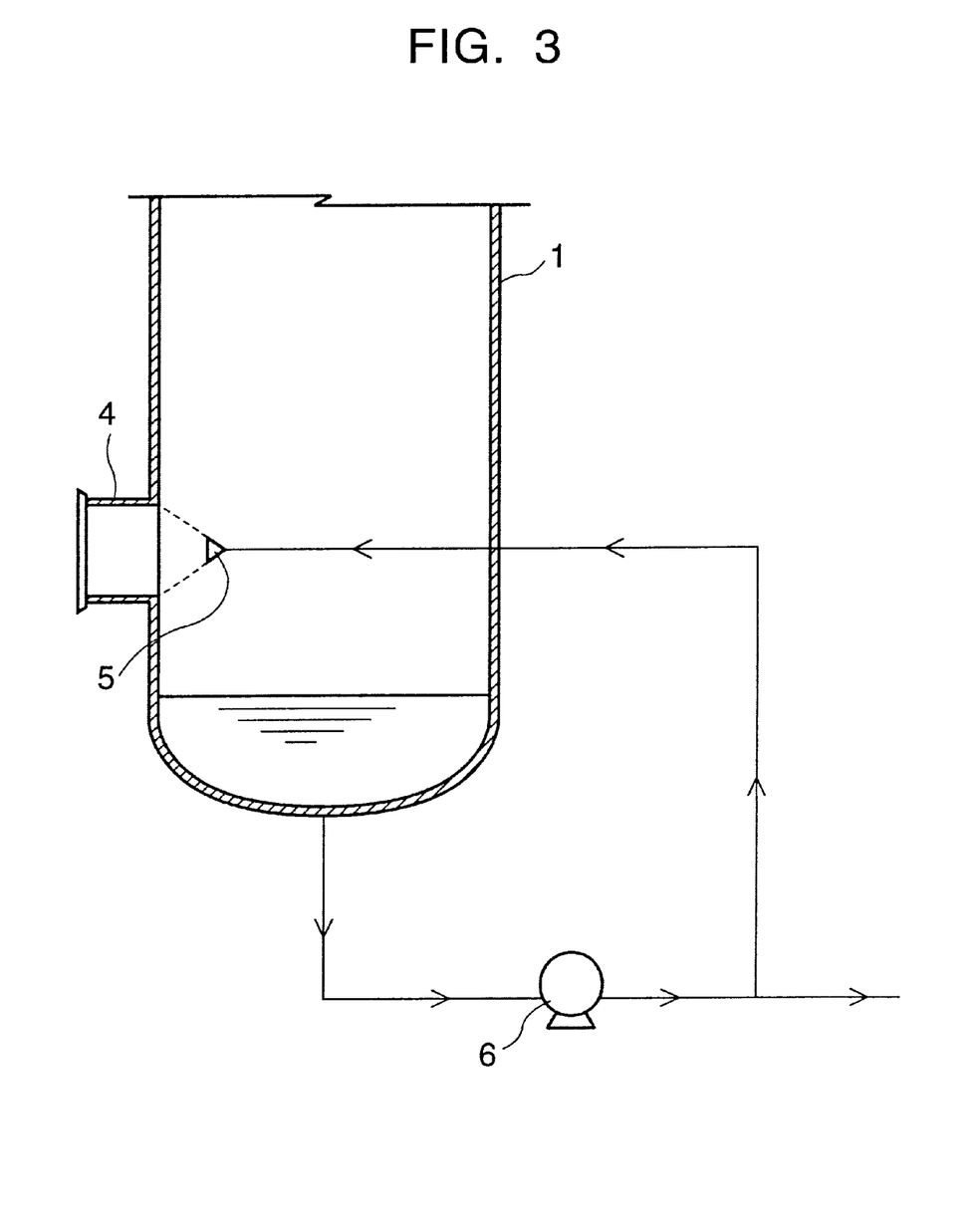
FIGS. 3 to 8 each are schematic diagrams illustrating an embodiment of the invented process for inhibiting the polymerization.
Figure 4:
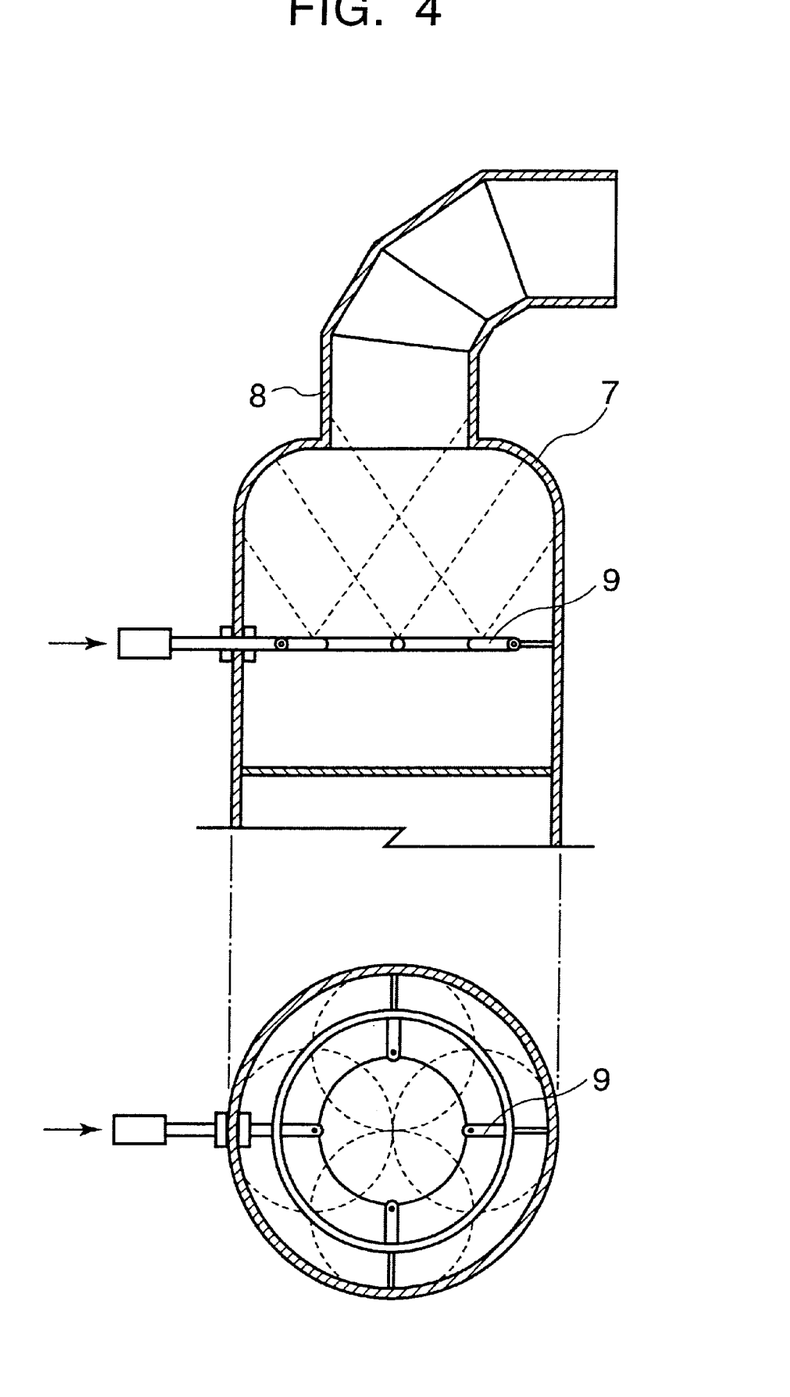
Figure 5:
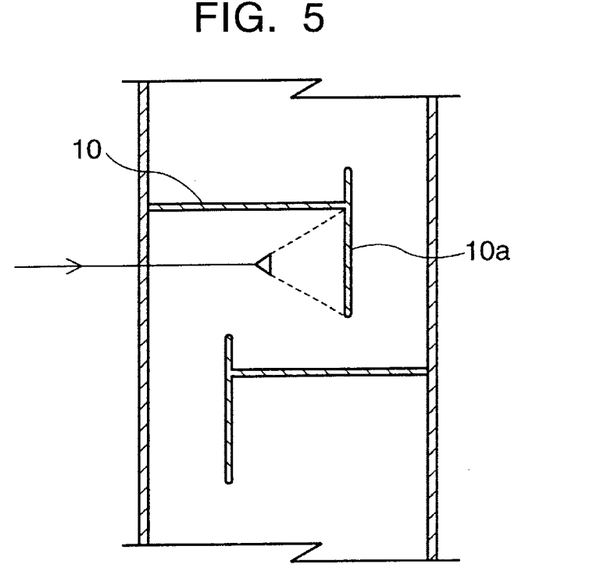
Figure 6:
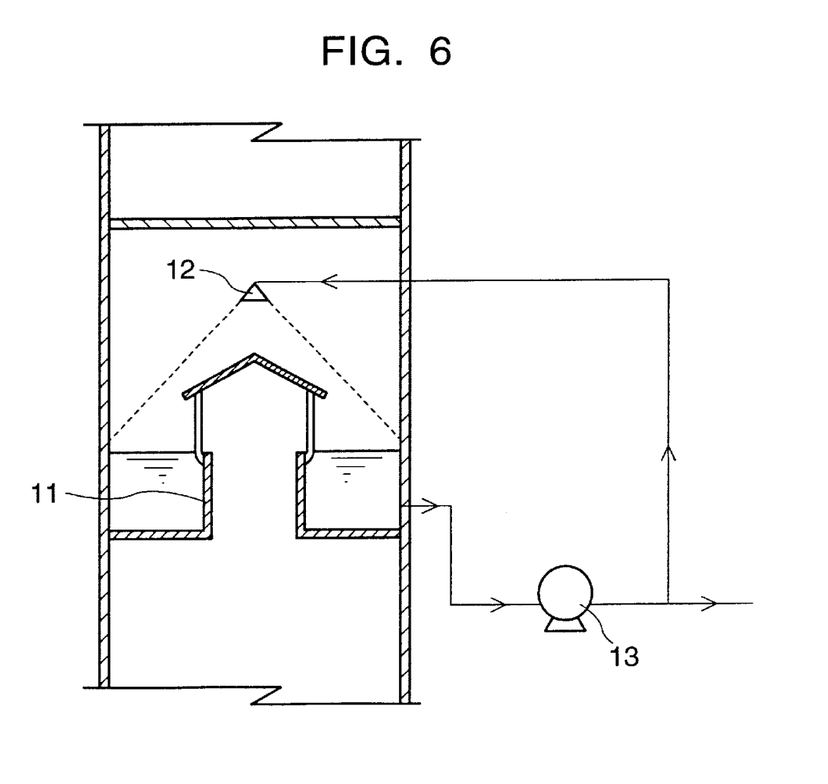
Figure 7:
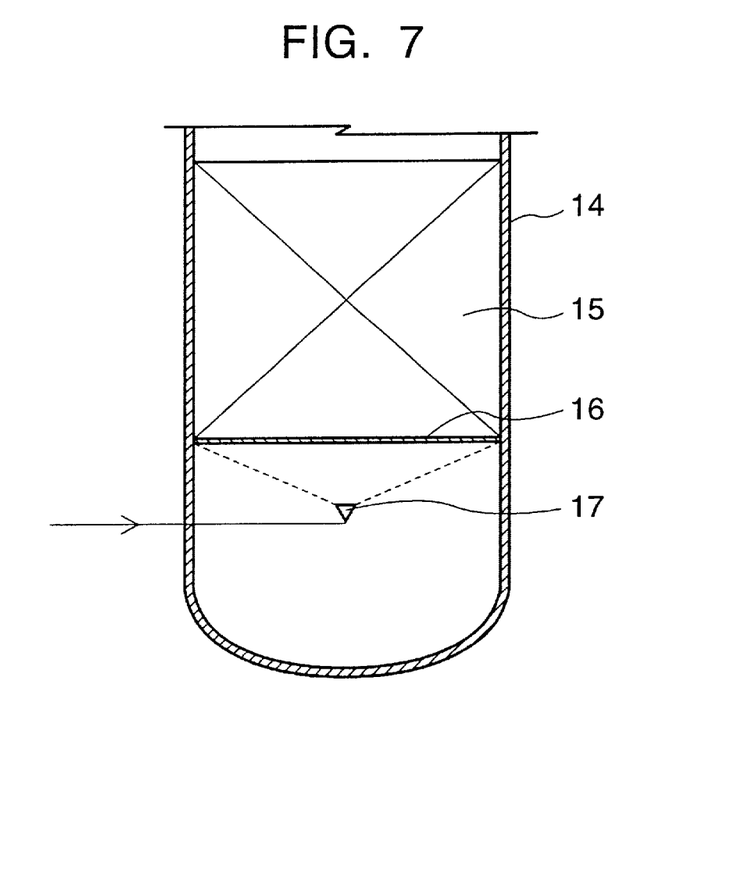
Figure 8:
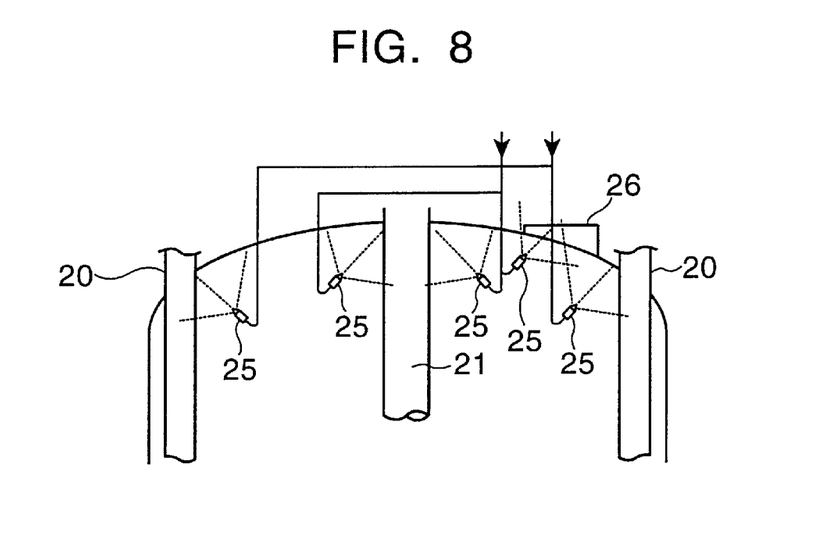

FIGS. 3 to 8 are schematic diagrams illustrating embodiments of the invention. FIG. 3 illustrates a process of returning a refined liquid withdrawn from the bottom of a distillation column 1 to the column, and spraying the returned refined liquid, by a spraying and supplying means 5, to a manhole 4 placed in a lower part of the distillation column 1. In a process shown in FIG. 4, a reflux liquid is sprayed by a spraying and supplying means 9 to an end plate 7 placed in the top and/or to a vapor line 8 connecting the top of the column with a condenser for use in a subsequent step. The spraying and supplying means 9 has four spray nozzles. FIG. 5 shows a process of spraying and putting a feedstock liquid into a downcomer 10a below a tray 10 of a plate distillation column. In a process shown in FIG. 6, a chimney 11 is provided to withdraw a liquid at some midpoint in a distillation column, and a portion of the withdrawn liquid is returned to the distillation column and is sprayed to the chimney 11 by a spraying and supplying means 12. FIG. 7 illustrates a process of spraying a liquid by a spraying and supplying means 17 to a supporting member 16 of a packed bed 15 in a packed distillation column 14. FIG. 8 shows a process of spraying a liquid by a spraying and supplying means 25 to an agitator 21, a baffle 20, and a manhole 26 in a reactor for reactive distillation. In these figures, each of the reference numerals 6 and 13 represents a pump. FIGS. 3 to 8 show embodiments of not only the inhibition of polymerization of a liquid formed by the condensation of a vapor in a vapor phase portion but also the inhibition of polymerization by dropping the spray liquid to a liquid phase portion to move the liquid thereby to shorten a retention time of the liquid on the surface of a constitutive member.

The invented process configured as described above can effectively inhibit the polymerization in distillation of easily polymerizable compounds such as (meth)acrylic acid and (meth)acrylic esters.

The present invention will now be illustrated in more detail with reference to several inventive examples and comparative examples below, which are not intended to limit the scope of the invention.

EXAMPLE 1

In this example, acrylic acid was purified by distillation using a stainless steel (SUS 316) distillation column including 50 stainless steel (SUS 316) sieve trays (inner diameter: 1300 mm) inside thereof. The distillation column was operated at the top temperature of 63° C., at the bottom temperature of 100° C., at an absolute pressure of 4.7 kPa (35 mmHg) and at a reflux ratio of 1.8. As polymerization inhibitors, 50 ppm of phenothiazine was added to a feed liquid, and 100 ppm of methoquinone was added to a reflux liquid. In addition, molecular oxygen (100%) was supplied from the bottom of the column in a proportion of 0.3% by volume relative to the volume of an overhead vapor (at standard temperature and pressure), and distillation was continuously performed under this condition.

In this procedure, a bottom circulation liquid of 90° C. was sprayed on the overall of a manhole (diameter: 500 mmφ) at the bottom of the column with a spray at a flow rate of 500 L/hr (wetting liquid rate: 2.5 m$^3$/m$^2$hr). As a result, the operation could be continued over about one month without trouble.

Comparative Example 1

Distillation was performed in the same manner as in Example 1, except that spraying to the manhole at the bottom of the column was not conducted. As a result, a liquid could not be significantly withdrawn from the bottom of the column after 8-day operation. The operation was stopped and an inspection was made to find that about 2 kg of polymer were attached to the bottom of the column and clogged a draw pipe at the bottom of the column.

EXAMPLE 2

Distillation was performed in the same manner as in Example 1, except that molecular oxygen was not supplied to the bottom of the column. As a result, a liquid could not be significantly withdrawn from the bottom of the column after 17-day operation. The operation was stopped and an inspection was made to find that about 1 kg of polymer were attached to the bottom of the column and clogged a draw pipe at the bottom of the column. The result in Example 2 indicates that supply of molecular oxygen is preferred even though the operation can be continued under this condition two times as long as that of Comparative Example 1.

EXAMPLE 3

Distillation was performed in the same manner as in Example 1, except that the liquid is sprayed at a temperature of 55° C. As a result, a noticeable amount of polymer was found in the withdrawn liquid after 25-day operation, and the operation was stopped to inspect the column. Polymer of about 0.5 kg was seen to be attached on the bottom of the column.

EXAMPLE 4

A reactive distillation for esterification of 2-ethylhexyl alcohol and acrylic acid was performed using a continuous feed stirred tank reactor and a distillation column. The continuous feed stirred tank reactor was made of a stainless steel (SUS 316) and had an inner diameter of 3500 mm and a shell height of 3500 mm. The distillation column was placed on the top of the reactor, was made of a stainless steel (SUS 316) and had an inner diameter of 1100 mm and a packing height (packing: CASCADE MINIRING 2P) of 5000 mm. The distillation column was operated at the top temperature of 43° C., at the top absolute pressure of 8 kPa and the reactor was operated at the temperature of 90° C. The reaction was catalyzed by an ion exchange resin. From the top of the column, 2-ethylhexyl alcohol containing 100 ppm of phenothiazine was fed, and from the top of the reactor, an acrylic acid solution containing 200 ppm of methoquinone was supplied. In addition, air was supplied from the bottom of the reactor in a proportion of 0.15% by volume relative to the volume of an overhead vapor at standard temperature and pressure, and the reactive distillation was continuously performed under this condition.

In this procedure, portions of a liquid withdrawn from the reactor were sprayed with a spray for two baffles (diameter: 200 mmφ) at a flow rate of 500 L/hr (wetting liquid rate: 1.6 $m^3/m^2hr$ in wetted length of 500 mm) per baffle, for two regions of an agitator (diameter 200 mmφ) at a flow rate of 500 L/hr (wetting liquid rate: 1.6 $m^3/m^2hr$ in wetted length of 500 mm) per region, and for an upper manhole (diameter: 500 mmφ) at a flow rate of 500 L/hr (wetting liquid rate: 2.5 $m^3/m^2hr$). As a result, the operation could be continued over about one month without trouble.

Comparative Example 2

Distillation was performed in the same manner as in Example 3, except that spraying operation was not conducted. As a result, polymer were observed in a withdrawn liquid from the reactor after 20-day operation. The operation was stopped and an inspection was made to find that about 2 kg of polymer were attached to the constitutive baffles, the agitator, and the manhole.

Other embodiments and variations will be obvious to those skilled in the art, and this invention is not to be limited to the specific matters stated above.

What is claimed is:

1. A method for inhibiting polymerization of an easily polymerizable compound contained in a liquid which is being distilled in a distillation apparatus, which method comprises spraying the liquid containing said easily polymerizable compound against a constitutive member of said apparatus, which constitutive member is surrounded by a liquid of substantially the same composition as the liquid being sprayed, while contacting the sprayed liquid in said distillation apparatus with a gas containing molecular oxygen to inhibit polymerization of said easily polymerizable compound and wherein said sprayed liquid has a temperature equal to or lower than that of the liquid surrounding said constitutive member.

2. The process according to claim 1, wherein a flow rate of liquid sprayed against said constitutive member is at least 0.5 $m^3/m^2$ hr with respect to the surface area of the constitutive member.

3. The process according to claim 1, wherein said liquid being sprayed contains a polymerization inhibitor.

4. The process according to claim 3, wherein said constitutive member is one selected from the group consisting of a tray supporting member, a packing supporting member, a flange, a nozzle, an end plate, a column wall, a chimney, a downcomer, a baffle, and a shaft of an agitator.

5. The process according to claim 3, wherein said easily polymerizable compound is a (meth)acrylic acid and/or a (meth)acrylic ester.

6. The process according to claim 1, wherein said constitutive member is a member selected from the group consisting of a tray supporting member, a packing supporting member, a flange, a nozzle, an end plate, a column wall, a chimney, a downcomer, a baffle, and a shaft of an agitator.

7. The process according to claim 1, wherein said easily polymerizable compound is a (meth)acrylic acid and/or a (meth)acrylic ester.

* * * * *